United States Patent [19]
Lahanas et al.

[11] Patent Number: 6,033,655
[45] Date of Patent: Mar. 7, 2000

[54] MAGNETIC COSMETIC COMPOSITIONS

[75] Inventors: Konstantinos M. Lahanas, Paramus, N.J.; Joseph Gubernick, New York; Gheorghe Cioca, Lake Grove, both of N.Y.

[73] Assignee: E-L Management Corp., New York, N.Y.

[21] Appl. No.: 09/044,502

[22] Filed: Mar. 19, 1998

Related U.S. Application Data

[63] Continuation-in-part of application No. 08/724,455, Oct. 1, 1996.

[51] Int. Cl.⁷ .............................. A61K 3/78; A61K 7/48
[52] U.S. Cl. ...................................... 424/78.1; 424/78.03
[58] Field of Search .............................. 424/78.1, 78.03, 424/78.26; 210/26

[56] References Cited

U.S. PATENT DOCUMENTS

| | | | |
|---|---|---|---|
| 2,718,489 | 9/1955 | Coonradt et al. | 210/26 |
| 3,389,080 | 6/1968 | Varden | 210/32 |
| 3,947,572 | 3/1976 | Borodkin | 424/78.1 |
| 4,150,173 | 4/1979 | Ziolo . | |
| 4,199,614 | 4/1980 | Ziolo . | |
| 4,238,558 | 12/1980 | Ziolo . | |
| 4,474,866 | 10/1984 | Ziolo . | |
| 5,160,725 | 11/1992 | Pilgrimm . | |
| 5,206,159 | 4/1993 | Cohen et al. . | |
| 5,358,659 | 10/1994 | Ziolo . | |
| 5,487,888 | 1/1996 | Mandeville, III et al. | 424/78.1 |
| 5,624,668 | 4/1997 | Lawrence et al. | 424/78.1 |

FOREIGN PATENT DOCUMENTS

| | | |
|---|---|---|
| 699964 A1 | 3/1996 | European Pat. Off. . |
| 3629761 | 3/1987 | Germany . |
| 5309016 | 11/1993 | Japan . |
| 9503061 A1 | 2/1995 | WIPO . |

*Primary Examiner*—Peter F. Kulkosky
*Attorney, Agent, or Firm*—Karen A. Lowney, Esq.

[57] ABSTRACT

The present invention relates to cosmetic or pharmaceutical compositions comprising a magnetic metal species bound to an ion exchange resin as well as a method for preparing stable compositions of this type.

5 Claims, No Drawings

MAGNETIC COSMETIC COMPOSITIONS

RELATED APPLICATIONS

This application is a continuation-in-part of copending U.S. Ser. No. 08/724,455, filed Oct. 1, 1996, the contents of which are incorporated herein by reference.

FIELD OF THE INVENTION

The present invention relates to a novel cosmetic compositions. More specifically, the invention relates to cosmetic compositions containing magnetic particles.

BACKGROUND OF THE INVENTION

The biological effects exerted by magnets have recently become very widely recognized. It is now widely accepted that exposure to a magnetic field can have a positive benefit on a variety of different types of products and on the consumer using such products so treated. For example, WO 9503061 discloses a preparation containing magnetic particles, which preparation can have the effect of increasing blood circulation, thereby purportedly enhancing delivery of active components to target tissues, among other effects. Exposure to a magnetic field is also said to have the effect of preserving food or cosmetic products, preventing the decay of materials contained therein (JP 5309016). It is also said that cosmetic products so treated, when applied to skin, can produce a "regenerative" action on the skin (DE 3629761). It is apparent, then, that those skilled in the art recognize that that treatment of products with a magnetic field can have a beneficial effect on the product and the end user.

Although the use of magnets to enhance activity or protect products is often achieved through incorporation of magnets in the packaging of the product, it may be desirable, where possible, to actually incorporate the magnetic material directly into the product. In the case of a cosmetic or topically applied pharmaceutical, for example, this permits the direct application to and retention on the skin of this active component. In order to provide the benefit to the consumer, however, the product must remain stable, and in addition, preferably also retains an attractive appearance without any obvious presence of metal particles. The present invention provides a composition which meets these requirements.

SUMMARY OF THE INVENTION

The present invention relates to stable cosmetic or pharmaceutical compositions comprising magnetic particles bound to ion exchange resin beads. These magnetic particles are transparent, thereby not interfering with the attractive appearance of the product as a whole. The invention also provides a method for preparing transparent magnetic particles which remain stable in a cosmetic or pharmaceutical composition, which method comprises combining a salt precursor of a magnetic metal oxide with ion exchange resin in an aqueous medium to form a slurry, contacting the slurry with a strong base to form a metal hydroxide bound to the resin beads, and rinsing the metal hydroxide/resin beads with a basic solution, to confer a basic pH to the bead composition.

DETAILED DESCRIPTION OF THE INVENTION

The compositions of the invention comprise transparent magnetic particles. Low optical density and transparent particles are known, having been used, for example as a carrier for reagents (U.S. Pat. No. 4,534,961), and as part of a xerographic toner or ink compositions (U.S. Pat. Nos. 5,358,659; 4,474,866; 4,238,558; 4,150,173; 4,199,614; 5,160,725; and EP 699964); the contents of each of these is incorporated herein by reference. However, their use in cosmetic and pharmaceutical compositions has not previously been suggested. Generally speaking, the particles are selected from cosmetically acceptable transition metals, such as iron, titanium, barium, nickel, cobalt, salts, carbonyls or oxides, thereof, or inorganic or organometallic complexes thereof, as well of mixtures of thereof, bound to an ion exchange resin. Particularly preferred starting materials are iron salts or oxides. The ion exchange resins to which the metals are bound should be selected from those which are cosmetically or pharmaceutically acceptable. It is possible to use anion exchange resins, for example, when the metal species is a metal-containing anion such as, for example, chloroplatinate, chloropalladate, or tetrachloroaurate. However, in most cases, the preferred resin will be a cation exchange resin; particularly preferred are dextran-based resins. Suitable resins are, for example, commercially available types such as Sephadex or Amberlite. The compounds are bound to the resin, using standard binding techniques, before they are combined with the appropriate carrier. For ease of mixing and application, as well as aesthetics, it is preferred that the resin be in the form of beads of approximately 1–1000µ in diameter.

A salt of the selected metal is added to the selected resin to form a slurry, and then contacted with an appropriate base to generate the desired metal-containing species. Alternately, the metal hydroxide can be taken up directly by any suitable means known in the art. In order to further process the magnetic beads for use in the final product, the metal containing bead is air oxidized. Air oxidation is preferable, as the use of stronger oxidation processes, while effective, can be detrimental to the integrity of the ion exchange resin.

Although the magnets prepared in this manner are effective and cosmetically/pharmaceutically acceptable, they are frequently unstable in compositions stored over prolonged periods of time and/or under extremes of temperature. Although air oxidation of the beads, as described above, is preferred, it is difficult to control the completeness of the oxidation. Therefore, if air oxidation of the magnetic particles is incomplete, the metal species of the magnet may continue to oxidize in the product. This in turn can lead to an increase in acidity, which can cause a deterioration in the resin and a concurrent deterioration of the product as a whole. Thus, in order to stabilize both the resin and the final product, it is desirable that the air-oxidized magnets be rinsed with a basic rinse after air oxidation. Preferably, the magnets are buffered to pH of about 8.5–10. Examples of useful buffers for this purpose are low molecular weight amines such as triethanolamine or aminomethylpropanol, phosphate buffers, carbonate buffers, or Tris buffers. Buffering techniques are of course well known in the art.

The buffering of the magnetic beads enhances their stability substantially. A comparison of otherwise identical products, one containing the magnets buffered with the basic rinse, and the other not so buffered, shows that after one month at 50° C., the product containing untreated magnets liquefies, while the product containing the buffered magnets retains its original fresh appearance.

The resin bound metal particles of the invention can be used in any type of cosmetic products in which the activity of a magnet is desired. As noted above, those skilled in the art recognize many biological activities for magnets, and the present composition can be used for any such purpose. The magnet-containing composition can be used as is, or in combination with a cosmetically or pharmaceutically acceptable carrier. In a particularly preferred embodiment, the addition of such magnets is used to enhance the moisturization capacity of a cosmetic product, or to reduce the harmful drying effects of a therapeutic product. To achieve this effect, the prepared magnetic particles are combined with a cosmetically or pharmaceutically acceptable carrier in an amount of about 0.0001–20%, more preferably about 2–10%, by weight of the composition as a whole. The term "pharmaceutically or cosmetically acceptable carrier" refers to a carrier, for either pharmaceutical or cosmetic use, which carrier delivers the active components to the intended target and which will not cause harm to humans or other recipient organisms. As used herein, "pharmaceutical" or "cosmetic" will be understood to encompass both human and animal pharmaceuticals or cosmetics. The magnet containing compositions can be prepared in any form convenient for topical application to the skin. Such forms include, but are not limited to gels, creams, dispersions, emulsions (water-in-oil or oil-in-water), suspensions, lotions, foams, mousses and the like. The magnets of the invention have been found to have a beneficial effect on the viscosity of emulsions.

Because of the skin enhancing effects of the magnet containing compositions of the present invention, they may also have incorporated active agents which are used for skin treatment, or which are routinely applied topically. Examples of such active agents which may form part of the composition include, but are not limited to, those that improve or eradicate age spots, keratoses and wrinkles, analgesics, anesthetics, antiacne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, sunscreens or hormones. More specific examples of useful active agents include retinoids, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinol, retinoic acid, 13-cis retinoic acid, hydrocortisone, hydrocortisone 21-acetate, hydrocortisone 17-valerate, hydrocortisone 17-butyrate, betamethasone valerate, betamethasone diproprionate, triamcinolone acetonide, fluocinonide, clobetasol, proprionate, benzoyl peroxide, crotamiton, propranolol, promethazine, vitamin A palmitate, vitamin E acetate, DHEA and derivatives thereof, alpha- or beta-hydroxy acids, and mixtures thereof. The amount of active agent to be used in any given formulation is readily determined in accordance with its usual dosage. Avoid extremes of pH, strongly oxidizing or reducing materials The formulation also can comprise other components which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine);

waterproofing agents (such as PVP/Eicosene Copolymer); water soluble film-formers (such as Hydroxypropyl methylcellulose);

oil-soluble film formers (such as Hydrogenated C-9 Resin); cationic polymers (such as Polyquaternium 10); anionic polymers (such as xanthan gum); vitamins (such as Tocopherol); and the like.

The invention is further illustrated in the following non-limiting examples.

EXAMPLES

Example 1

An iron-based magnetic particle composition is prepared as follows: To 500 g $H_2O$ is added 5 g $FeCl_2.4H_2O$. This mixture is filtered to remove resulting debris, and after filtration, is blended with 10 g Sephadex SP-C50 to form a slurry. The slurry is then added to 500 g 5% NaOH solution. The resulting product is again filtered, then washed and filtered several times to remove any residual hydroxide, producing a product in which $Fe(OH)_2$ is bound to Sephadex beads.

The particle composition, as a slurry, is allowed to stand at room temperature, typically for about one hour, to accomplish air oxidation. The slurry is then weighed on a standard scale and rinsed with an equal amount of 0.25% triethanolamine to achieve a pH of about 9. At this point, they are ready to be incorporated into a product.

What we claim is:

1. A method of moisturizing the skin which comprises applying to the skin a cosmetic or pharmaceutical composition containing a stable transparent magnetic particle composition prepared by contacting a magnetic iron metal species with an ion exchange resin under conditions which permit binding between the metal and the resin, and rinsing the metal-bound resin with a basic rinse to achieve a pH of about 8.5–10.0.

2. The method of claim 1 in which the resin is a cation exchange resin.

3. The method of claim 1 in which the metal is an iron compound and the resin is a dextran-based resin.

4. The method of claim 1 in which the composition comprises from 0.0001–20% by weight of a magnetic iron species bound to a cation exchange resin.

5. The method of claim 4 in which the composition is in the form of a gel, cream, dispersion, emulsion, suspension, lotion, foam, or a mousse.

* * * * *